United States Patent
Lee et al.

(10) Patent No.: US 10,523,066 B2
(45) Date of Patent: Dec. 31, 2019

(54) WIRELESS POWER TRANSMISSION METHOD AND APPARATUS

(71) Applicant: Samsung Electronics Co., Ltd., Suwon-si (KR)

(72) Inventors: Wonseok Lee, Yongin-si (KR); Jaechun Lee, Seoul (KR); Young-Jun Hong, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 165 days.

(21) Appl. No.: 15/680,390

(22) Filed: Aug. 18, 2017

(65) Prior Publication Data

US 2018/0175677 A1 Jun. 21, 2018

(30) Foreign Application Priority Data

Dec. 21, 2016 (KR) .................. 10-2016-0175827

(51) Int. Cl.
*H02J 50/90* (2016.01)
*H02J 50/10* (2016.01)
*H02J 7/02* (2016.01)
*H04B 5/00* (2006.01)
*H02J 50/80* (2016.01)
*A61N 1/378* (2006.01)

(52) U.S. Cl.
CPC ............. *H02J 50/90* (2016.02); *H02J 7/025* (2013.01); *H02J 50/10* (2016.02); *H02J 50/80* (2016.02); *H04B 5/0031* (2013.01); *H04B 5/0037* (2013.01); *A61B 2560/0219* (2013.01); *A61M 2205/8287* (2013.01); *A61N 1/3787* (2013.01)

(58) Field of Classification Search
CPC .. H02J 50/10; H02J 50/80; H02J 50/90; H02J 7/025; H04B 5/0031; H04B 5/0037; A61B 2560/0219; A61M 2205/8287; A61N 1/3787
USPC ......................................... 307/104
See application file for complete search history.

(56) References Cited

U.S. PATENT DOCUMENTS

| | | |
|---|---|---|
| 7,613,497 B2 | 11/2009 | Govari et al. |
| 7,774,069 B2 | 8/2010 | Olson et al. |
| 8,078,286 B2 | 12/2011 | Govari et al. |
| 9,044,617 B2 | 6/2015 | Aghassian |
| 2014/0091641 A1* | 4/2014 | Ichikawa ........... B60L 53/65 307/104 |
| 2015/0238118 A1 | 8/2015 | Legassey et al. |

FOREIGN PATENT DOCUMENTS

| | | |
|---|---|---|
| JP | 2015-111996 A | 6/2015 |
| JP | 2016-111791 A | 6/2016 |
| KR | 10-2013-0028446 A | 3/2013 |
| KR | 10-2016-0025200 A | 3/2013 |
| KR | 10-1257676 B1 | 5/2013 |
| KR | 10-1659080 B1 | 9/2016 |
| KR | 10-2018-0055069 A | 5/2018 |

* cited by examiner

*Primary Examiner* — Hal Kaplan
(74) *Attorney, Agent, or Firm* — NSIP Law

(57) ABSTRACT

A wireless power transmission method and apparatus are provided. The wireless power transmission method receives a signal associated with a relative position of the wireless power transmission based on a frequency in a high frequency band, and determines whether to wirelessly transmit a power based on an intensity of the received signal.

18 Claims, 7 Drawing Sheets

WIRELESS POWER TRANSMISSION METHOD AND APPARATUS

CROSS-REFERENCE TO RELATED APPLICATION(S)

This application claims the benefit under 35 USC § 119(a) of Korean Patent Application No. 10-2016-0175827, filed on Dec. 21, 2016, in the Korean Intellectual Property Office, the entire disclosure of which is incorporated herein by reference for all purposes.

BACKGROUND

1. Field

The following description relates to wireless power transmission.

2. Description of Related Art

A wireless device designed to be inserted inside a body of a human or an animal typically includes a reception coil. The wireless device may wirelessly receive power from a wireless power transmission apparatus by an interaction with a transmission coil of the wireless power transmission apparatus. An efficiency of the power transmission typically varies depending on the relative positions of the transmission coil and the reception coil and the direction of each of the transmission coil and the reception coil.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A wireless power transmission method performed by a wireless power transmission apparatus includes receiving a first signal having a first frequency from an implantable device, determining whether a magnitude of the first signal satisfies a first criterion, and wirelessly transmitting power to the implantable device based on a second signal having a second frequency in response to the magnitude of the first signal satisfying the first criterion.

The wireless power transmission method may include re-receiving the first signal from the implantable device when the wireless power transmission apparatus is moved to another position relative to the implantable device in response to the magnitude of the first signal not satisfying the first criterion.

The first frequency may be greater than the second frequency.

The wireless power transmission method may further include measuring an impedance variation of a first position information reception circuit in the wireless power transmission apparatus in response to a position adjustment signal being received from the implantable device and determining whether the impedance variation satisfies a second criterion. The position adjustment signal may be generated by the implantable device in response to the transmitted power being less than a third criterion.

The wireless power transmission method may further include interrupting a wireless power transmission in response to the impedance variation not satisfying the second criterion.

The wireless power transmission method may further include outputting a position adjustment request signal indicating a first distance in response to the impedance variation not satisfying the second criterion.

The wireless power transmission method may further include outputting a position adjustment request signal indicating a second distance in response to the impedance variation satisfying the second criterion.

A wireless power reception method performed by an implantable device includes transmitting a first signal having a first frequency to a wireless power transmission apparatus and receiving power from the wireless power transmission apparatus based on a second signal having a second frequency.

The first frequency may be greater than the second frequency.

The wireless power reception method may further include determining whether the received power satisfies a third criterion.

The wireless power reception method may further include charging a battery of the implantable device with the received power in response to the received power satisfying the third criterion.

The wireless power reception method may further include transmitting a position adjustment signal to the wireless power transmission apparatus in response to the received power not satisfying the third criterion.

A non-transitory computer-readable storage medium may store instructions for causing computing hardware to perform the wireless power transmission method.

A wireless power transmission apparatus includes a first position information reception circuit configured to receive a first signal having a first frequency from an implantable device, a wireless power transmission circuit configured to transmit a second signal having a second frequency to the implantable device, and a control circuit configured to determine whether a magnitude of the first signal satisfies a preset first criterion and to wirelessly transmit a power to the implantable device based on the second signal in response to the magnitude of the first signal satisfying the first criterion.

The wireless power transmission apparatus may include a coil configured to transmit and receive the first signal and the second signal through coupling with the implantable device.

The wireless power transmission apparatus may include a second position information reception circuit configured to receive a third signal having a third frequency corresponding to a position adjustment from the implantable device.

The wireless power transmission apparatus may include a data reception circuit configured to receive a fourth signal of a fourth frequency including data from the implantable device.

The wireless power transmission apparatus may further include a blocking circuit configured to block an interference between the first position information reception circuit and the wireless power transmission circuit.

Other features and aspects will be apparent from the following detailed description, the drawings, and the claims.

Figure 1:
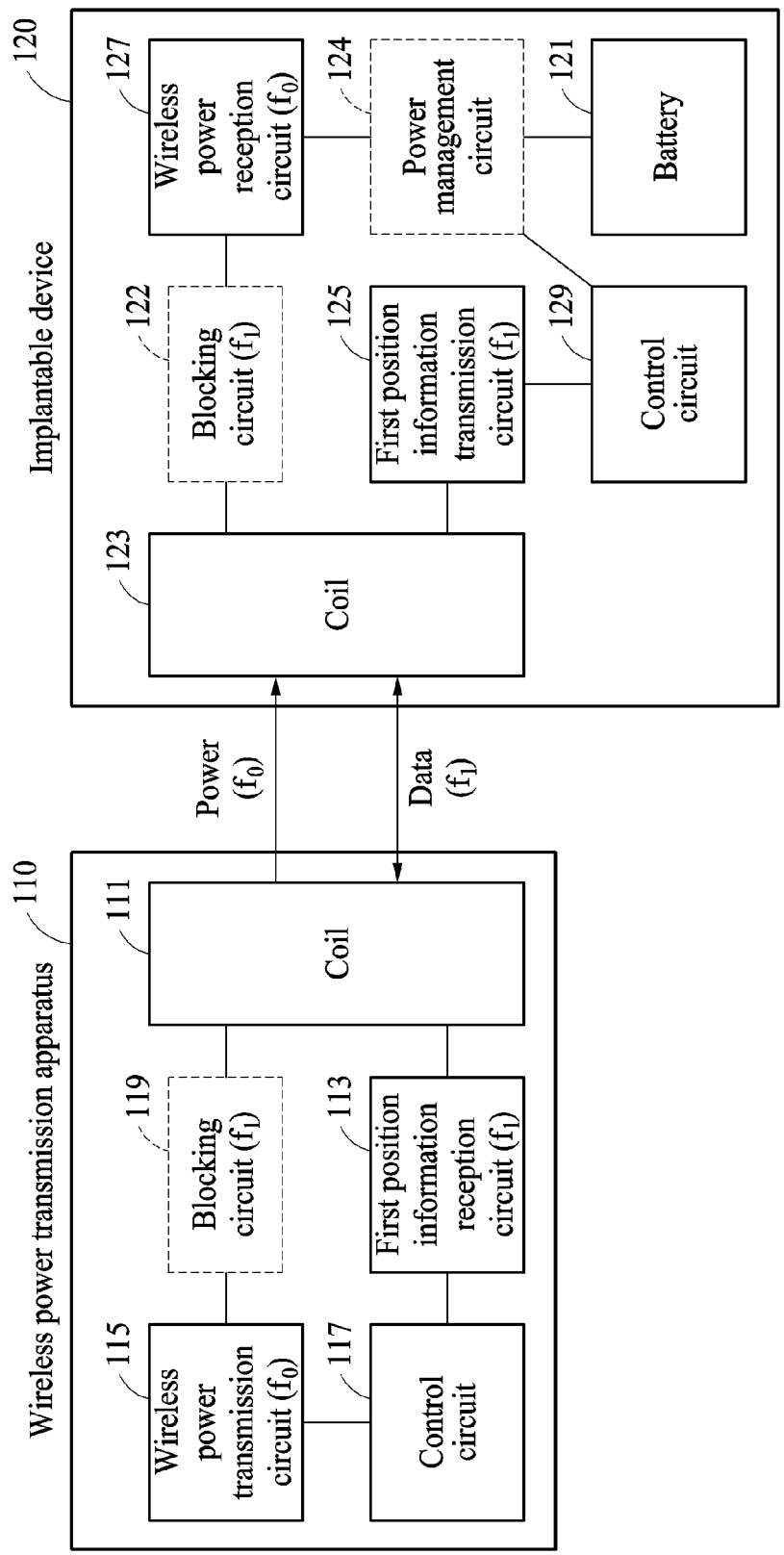
FIG. 1 illustrates an example of a configuration of a system for wirelessly transmitting power.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The following structural or functional descriptions are examples to merely describe the examples, and the scope of the examples is not limited to the descriptions provided in the present specification.

Although terms of "first" or "second" are used to explain various components, the components are not limited to the terms. These terms should be used only to distinguish one component from another component. For example, a "first" component may be referred to as a "second" component, or similarly, and the "second" component may be referred to as the "first" component within the scope of the right according to the concept of the present disclosure.

It will be understood that when a component is referred to as being "connected to" another component, the component can be directly connected or coupled to the other component or intervening components may be present.

As used herein, the singular forms are intended to include the plural forms as well, unless the context clearly indicates otherwise. It should be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood. Terms defined in dictionaries generally used should be construed to have meanings matching with contextual meanings in the related art and are not to be construed as an ideal or excessively formal meaning unless otherwise defined herein.

Hereinafter, examples will be described in detail with reference to the accompanying drawings, and like reference numerals in the drawings refer to like elements throughout.

FIG. 1 illustrates an example of a configuration of a system for wirelessly transmitting power. In the present description, a system for wirelessly transmitting power may be referred to as a "wireless power transmission system."

An implantable device 120 may be contained within a body of a human or an animal and may perform a task such as assisting a biofunction of the user or acquiring biometric information. The implantable device 120 includes a battery as an energy source. The battery is charged by an external device, because the battery has finite energy. As such, a wireless charging scheme is used to charge the battery. A position of the implantable device 120 should therefore be identified since the implantable device 120 is contained within the body of a human or an animal.

A wireless power transmission apparatus 110 wirelessly transmits power to the implantable device 120 while determining a position of the implantable device 120 based on different frequencies.

The wireless power transmission apparatus 110 is used to charge, for example, an implantable biometric recognition device for recognition based on a physical characteristic and/or a behavioral characteristic. The physical characteristic may include, for example, a fingerprint, a face, an iris, a vascular pattern, a hand geometry, deoxyribonucleic acid (DNA), etc. The behavioral characteristic may include, for example, a gait, a voiceprint, a dynamic signature, etc.

The wireless power transmission apparatus 110 may be used to charge an implantable biometric information collection device for collecting biometric information, for example, an electromyographic (EMG) signal, a respiration rate, a skin temperature, a skin conductance, a pulse, a heart rate, a blood oxygen concentration, etc. Additionally, or alternatively, the wireless power transmission apparatus 110 may be used to charge an implantable biofunction assist device for assisting a body movement or the workings of an organ in a body. The implantable biofunction assist device may include, for example, an artificial heart, a pacemaker (for example, an implantable cardioverter-defibrillator (ICD)), a deep brain neurostimulator, a cochlear implant (CI), an insulin pump, etc.

Referring to FIG. 1, the wireless power transmission system includes the wireless power transmission apparatus 110 and the implantable device 120. The wireless power transmission apparatus 110 includes a coil 111, a first position information reception circuit 113, a wireless power transmission circuit 115, and a control circuit 117. The wireless power transmission apparatus 110 may further include a blocking circuit 119.

The wireless power transmission apparatus 110 and the implantable device 120 use a plurality of frequency bands. A frequency $f_0$ in a low frequency band is used to transmit power. A frequency $f_1$ in a high frequency band is used to transmit data. The data includes position information about the relative positions of the wireless power transmission apparatus 110 and the implantable device 120.

For example, the frequency $f_0$ includes a longwave or low frequency (LF) in a frequency band of 3 kilohertz (kHz) to 300 kHz, or a shortwave or high frequency (HF) in a frequency band of 3 megahertz (MHz) to 300 MHz. For example, the frequency $f_1$ includes an ultra-high frequency (UHF) in a frequency band of 0.3 gigahertz (GHz) to 3 GHz. However, the above frequencies are merely an example, and the frequencies $f_1$ and $f_0$ may be in the other frequency bands. In the following description, the frequencies $f_1$ and $f_0$ are referred to as a "first frequency" and a "second frequency," respectively. The first frequency is higher than the second frequency.

The frequency $f_0$ allows a signal to be transferred within a short distance threshold through biological tissue when the implantable device 120 is implanted in a living subject. The frequency $f_1$ allows a signal to be transferred over a long distance through biological tissue, when the implantable device 120 is implanted in a living subject, because the frequency $f_1$ has a strong straightness. The short distance and the long distance are relative distances, and an absolute distance is determined based on, for example, a thickness of a biological tissue that the signal is transferred through.

The implantable device 120 uses a single coil 123 to transmit or receive signals in a plurality of frequency bands. Because the single coil 123 is used, a volume of the implantable device 120 is reduced. The wireless power transmission apparatus 110 also uses a single coil, that is, the coil 111, to transmit or receive signals in a plurality of frequency bands. Because the coil 111 is used, a volume of the wireless power transmission apparatus 110 is reduced. For example, because the wireless power transmission apparatus 110 is not inserted into a body, the volume is not significantly restricted, and separate coils are used for each frequency band.

Each of the coils 111 and 123 includes a passive element on which a wire with an inductance is wound, and includes a plurality of loops. Each of the loops may have a circular shape, however, is not limited thereto. For example, each of the loops has a polygonal shape. The coils 111 and 123 may be, for example, antennas, and may receive magnetic flux in a direction corresponding to a central axis of each of the coils 111 and 123. The coils 111 and 123 may generate a current flow in response to the magnetic flux being received. The coils 111 and 123 may generate an electromagnetic wave by changing current in response to a change in the magnetic flux. As shown in FIG. 1, the coils 111 and 123 transmit power or data between the implantable device 120 and the wireless power transmission apparatus 110.

The first position information reception circuit 113 receives a first signal having a first frequency from the implantable device 120. For example, the implantable device 120 transmits the first signal by periodically changing a current flow in the coil 123 based on the first frequency. By the first signal, a current corresponding to the first frequency is induced to flow in the coil 111. The induced current is received by the first position information reception circuit 113 and the first position information reception circuit 113 receives the first signal.

The wireless power transmission circuit 115 wirelessly transmits power to a wireless power reception circuit 127 of the implantable device 120 based on a second signal having a second frequency. For example, the wireless power transmission apparatus 110 transmits the second signal by periodically changing a current flow in the coil 111 based on the second frequency.

The control circuit 117 determines whether a magnitude of the first signal satisfies a preset first criterion. When the magnitude of the first signal satisfies the first criterion, the control circuit 117 wirelessly transmits power to the implantable device 120 based on the second signal.

The blocking circuit 119 allows the second signal to be transmitted from the wireless power transmission circuit 115 to the coil 111. For example, a current corresponding to the second signal passes through the blocking circuit 119. In this example, the blocking circuit 119 is connected to a portion of a loop among the plurality of loops of the coil 111, and transmits the second signal using the portion of the loop. The blocking circuit 119 blocks the first signal from being transmitted to the wireless power transmission circuit 115. That is, the blocking circuit 119 blocks a current flow corresponding to the first signal. In this example, the blocking circuit 119 blocks a current generated in response to the first signal being received to the first position information reception circuit 113 through the portion of the loop from flowing into the wireless power transmission circuit 115, and accordingly it is possible to prevent power consumption and an interference phenomenon. For example, the blocking circuit 119 is a circuit configured to open an electrical connection in response to the first signal being received and to close an electrical connection in response to the second signal being received.

Referring to FIG. 1, the implantable device 120 includes a battery 121, the coil 123, a first position information transmission circuit 125, the wireless power reception circuit 127 and a control circuit 129. The implantable device 120 may further include a blocking circuit 122 or a power management circuit 124.

The first position information transmission circuit 125 transmits the first signal of the first frequency to the wireless power transmission apparatus 110. For example, the first position information transmission circuit 125 transmits the first signal by periodically changing a current flow in the coil 123 based on the first frequency.

The wireless power reception circuit 127 receives power from the wireless power transmission apparatus 110 based on the second signal of the second frequency. For example, the wireless power transmission apparatus 110 transmits the second signal by periodically changing a current flow in the coil 111 based on the second frequency. By the second signal, a current corresponding to the second frequency is induced to flow in the coil 123. The induced current is received by the wireless power reception circuit 127 and the wireless power reception circuit 127 receives the second signal.

The power management circuit 124 acquires power from energy included in the second signal. The power management circuit 124 determines whether a power of the battery 121 is discharged or whether the battery 121 is overcharged. When the power of the battery 121 is discharged, the power management circuit 124 charges the battery 121. When charging of the battery 121 is completed, the power management circuit 124 interrupts the charging of the battery 121.

The control circuit 129 transmits the first signal to the wireless power transmission apparatus 110 and receives the power from the wireless power transmission apparatus 110 based on the second signal.

The blocking circuit 122 allows the second signal to be transmitted from the coil 123 to the wireless power reception circuit 127. For example, a current corresponding to the second signal passes through the blocking circuit 122. The blocking circuit 122 blocks the first signal from being transmitted to the wireless power reception circuit 127. For example, the blocking circuit 122 blocks a current flow corresponding to the first signal. The blocking circuit 122 blocks a current generated in response to the first signal being transmitted from the first position information transmission circuit 125 through a portion of a loop included in the coil 123 from flowing into the wireless power reception circuit 127, and accordingly it is possible to prevent a power consumption and an interference phenomenon.

The wireless power transmission apparatus 110 and the implantable device 120 use a high frequency band with a strong straightness to transmit position information, separately from a low frequency band to transmit power, and accordingly, the wireless power transmission apparatus 110 may gradually determine a position of the implantable device 120 from a long distance. The position of the implantable device 120 may be, therefore, accurately determined, and it may be possible to realize an accurate alignment between the wireless power transmission apparatus 110 and the implantable device 120 and to enhance an efficiency of a wireless power transmission.

Figure 2:
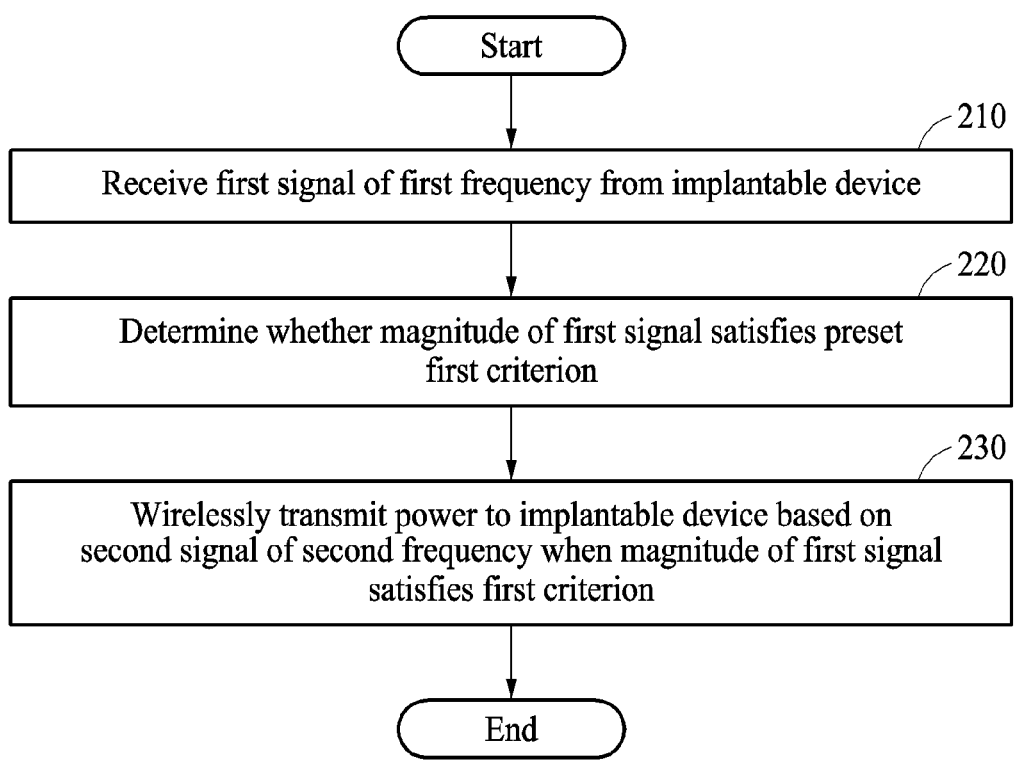
FIG. 2 is a flowchart illustrating an example of a wireless power transmission method.

FIG. 2 illustrates an example of a wireless power transmission method.

The wireless power transmission method of FIG. 2 is performed by, for example, the wireless power transmission system of FIG. 1.

Referring to FIG. 2, in operation 210, the wireless power transmission apparatus 110 receives a first signal having a first frequency from the implantable device 120. The first frequency may be a frequency in a high frequency band, and includes, for example, a UHF. The first signal may have a strong straightness due to a characteristic of a high frequency, and may be received by the wireless power transmission apparatus 110 from a long distance.

To determine a magnitude of the first signal, a distance between the wireless power transmission apparatus 110 and the implantable device 120 is used. The magnitude of the first signal decreases in response to the distance increasing, and increases in response to the distance decreasing. For example, when the wireless power transmission apparatus 110 approaches the implantable device 120, the magnitude of the first signal slightly changes. A first criterion is set as a magnitude of the first signal received by the wireless power transmission apparatus 110 when the wireless power transmission apparatus 110 is located at a boundary between a short distance and a long distance.

In operation 220, the wireless power transmission apparatus 110 determines whether the magnitude of the first signal satisfies the first criterion. The wireless power transmission apparatus 110 determines, for example, based on the magnitude of the first signal, whether the distance between the wireless power transmission apparatus 110 and the implantable device 120 decreases. Determining that the magnitude of the first signal is greater than the first criterion indicates that the distance between the wireless power transmission apparatus 110 and the implantable device 120 is less than the short distance threshold.

The magnitude of the first signal includes, for example, a magnitude of a voltage, a current, or a power corresponding to the first signal. When a magnitude of a voltage, a current, or a power corresponding to the first signal transmitted by the implantable device 120 is calculated, the magnitude of the first signal may also include a voltage ratio, a current ratio, or a power ratio, respectively, of the received first signal to the transmitted first signal.

In operation 230, the wireless power transmission apparatus 110 wirelessly transmits power to the implantable device 120 based on a second signal having a second frequency, when the magnitude of the first signal satisfies the first criterion. For example, when the distance between the wireless power transmission apparatus 110 and the implantable device 120 is less than the short distance threshold, the second signal is transmitted to the implantable device 120. In this example, the implantable device 120 receives the second signal.

Figure 3:
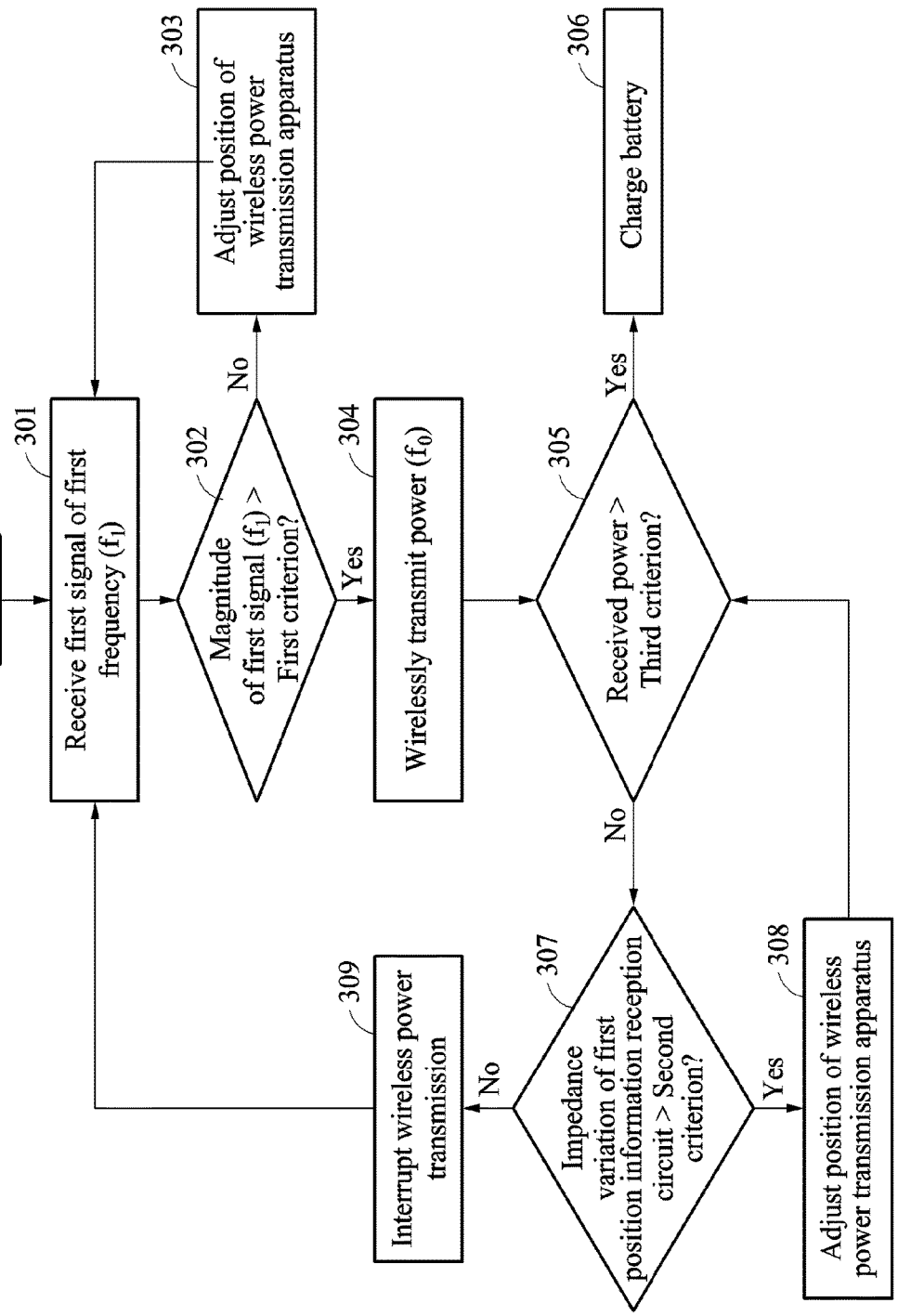
FIG. 3 is a flowchart illustrating an example of a process of wirelessly transmitting power.

FIG. 3 illustrates an example of a process for wirelessly transmitting power.

The process of FIG. 3 is performed by, for example, the wireless power transmission system of FIG. 1.

Referring to FIG. 3, in operation 301, the implantable device 120 transmits a first signal having a first frequency to the wireless power transmission apparatus 110, and the wireless power transmission apparatus 110 receives the first signal from the implantable device 120.

In operation 302, the wireless power transmission apparatus 110 determines whether a magnitude of the first signal satisfies a preset first criterion, for example, whether the magnitude of the first signal is greater than the first criterion. Determining that the magnitude of the first signal satisfies the first criterion indicates that the wireless power transmission apparatus 110 is approaching the implantable device 120, and that the wireless power transmission apparatus 110 and the implantable device 120 are at a distance that is less than a short distance threshold from each other.

The wireless power transmission apparatus 110 outputs information about whether the magnitude of the first signal satisfies the first criterion. The wireless power transmission apparatus 110 includes an output device, for example, a light emitting diode (LED), a display device, an acoustic device, a vibrating device, etc. For example, when the magnitude of the first signal satisfies the first criterion, an LED included in the wireless power transmission apparatus 110 may blink twice. Conversely, when the magnitude of the first signal does not satisfy the first criterion, the LED may blink once.

In operation 303, the wireless power transmission apparatus 110 re-receives the first signal from the implantable device 120 at a new, adjusted position of the wireless power transmission apparatus 110, when the magnitude of the first signal does not satisfy the first criterion. For example, a user may adjust the position of the wireless power transmission apparatus 110 in response to seeing that the LED blinks once. The wireless power transmission apparatus 110 located at the adjusted position re-receives the first signal from the implantable device 120. By moving the wireless transmission apparatus 110 to an adjusted position, the wireless power transmission apparatus 110 induces the implantable device 120 to be located within the short distance threshold. Although it is described above that the wireless transmission apparatus 110 is being moved towards the implantable device 120, either one, or both of the wireless transmission apparatus 110 and the implantable device 120 may be moved to decrease the distance between wireless transmission apparatus 110 and implantable device 120.

In operation 304, the wireless power transmission apparatus 110 wirelessly transmits power to the implantable device 120 via a second signal having a second frequency, when the magnitude of the first signal satisfies the first criterion. Operation 304 is an operation of transmitting the second signal for a fine position adjustment, and may not be used for transmitting power in earnest.

In operation 305, the implantable device 120 receives the power from the wireless power transmission apparatus 110 based on the second signal, and determines whether the received power satisfies a preset third criterion, for example, whether the received power is greater than the third criterion. Determining that the received power satisfies the third criterion indicates that the wireless power transmission apparatus 110 and the implantable device 120 are optimally aligned. The third criterion is set to a strength of power suitable for battery charging. The implantable device 120 determines whether to initiate charging of a battery based on the received power, or whether to provide a notification of a fine adjustment of the position of the wireless power transmission apparatus 110 and/or the implantable device 120.

In operation 306, the implantable device 120 charges a battery of the implantable device 120 with the received power, when the received power satisfies the third criterion. When power of the battery of the implantable device 120 is discharged, the implantable device 120 initiates charging of the battery. When the charging of the battery is completed, the implantable device 120 interrupts the charging.

The implantable device 120 may include a protection circuit module (PCM). For example, when the battery is overcharged, the implantable device 120 may activate the PCM to protect the battery and to prevent a damage of a body structure.

When the received power does not satisfy the third criterion, the implantable device 120 transmits a position adjustment signal to the wireless power transmission apparatus 110. The position adjustment signal may be a signal indicating that the position of the wireless power transmission apparatus 110 needs to be finely adjusted. For example, the implantable device 120 transmits the position adjustment signal using the first frequency.

In operation 307, the wireless power transmission apparatus 110 measures an impedance variation of a first position information reception circuit included in the wireless power transmission apparatus 110 in response to the position adjustment signal being received from the implantable device 120. Because the first signal corresponds to a high frequency band, the magnitude of the first signal is saturated in a short distance between the wireless power transmission apparatus 110 and the implantable device 120. The magnitude of the first signal slightly changes within the short distance threshold, and accordingly is not suitable for a fine position adjustment within the short distance threshold. The impedance variation has a relatively high value based on a change in a distance between the wireless power transmission apparatus 110 and the implantable device 120 even within the short distance threshold. Accordingly, the position of the wireless power transmission apparatus 110 is adjusted in the short distance threshold based on the impedance variation.

In operation 307, the wireless power transmission apparatus 110 determines whether the impedance variation satisfies a preset second criterion, for example, whether the impedance variation is greater than the second criterion. The impedance variation is a difference between an impedance of the first position information reception circuit measured at a current position of the wireless power transmission apparatus 110 and an impedance of the first position information reception circuit measured when the wireless power transmission apparatus 110 is located far away from the implantable device 120. The second criterion is set to a difference between an impedance of the first position information reception circuit measured at a position suitable for a wireless power transmission and the impedance measured when the wireless power transmission apparatus 110 is located far away from the implantable device 120.

For example, the wireless power transmission apparatus 110 determines whether an impedance change rate satisfies a preset second criterion. The impedance change rate is a rate of an impedance change per unit length when the wireless power transmission apparatus 110 moves, and may be referred to as a "sensitivity of an impedance change." The wireless power transmission apparatus 110 may use the sensitivity of the impedance change based on a movement of the wireless power transmission apparatus 110 for the fine position adjustment. In this example, the second criterion is a minimum sensitivity of the impedance change suitable for the fine position adjustment.

The wireless power transmission apparatus 110 outputs information about whether the impedance variation or the impedance change rate satisfies the second criterion. For example, to notify a user of the information about whether the impedance variation or the impedance change rate satisfies the second criterion, the wireless power transmission apparatus 110 uses an LED, a display device, an acoustic device, a vibrating device, etc., as an output device.

In operation 308, the wireless power transmission apparatus 110 outputs a position adjustment request signal of a second distance, when the impedance variation satisfies the second criterion. The second distance may correspond to a fine position change within the short distance threshold. Accordingly, a user may finely adjusts the position of the wireless power transmission apparatus 110 and/or the implantable device 120. When the position is adjusted, operation 305 is repeated. The above process is repeated until the power received to the implantable device 120 satisfies the third criterion.

In operation 309, the wireless power transmission apparatus 110 interrupts the wireless power transmission, when the impedance variation does not satisfy the second criterion. Also, the wireless power transmission apparatus 110 may output a position adjustment request signal of a first distance. The first distance may correspond to a greater position change compared to the second distance. Accordingly, a user may perform a large adjustment of the position of the wireless power transmission apparatus 110 and/or the implantable device 120. When the position is adjusted, operations beginning at 301 are reperformed to determine whether the wireless power transmission apparatus 110 is in a position to transfer power to the implantable device 120.

Although not shown in FIG. 3, if charging of a battery 306 is interrupted, operations beginning at 301 may be reperformed to determine whether the wireless power transmission apparatus 110 is in a position to transfer power to the implantable device 120.

Figure 4:
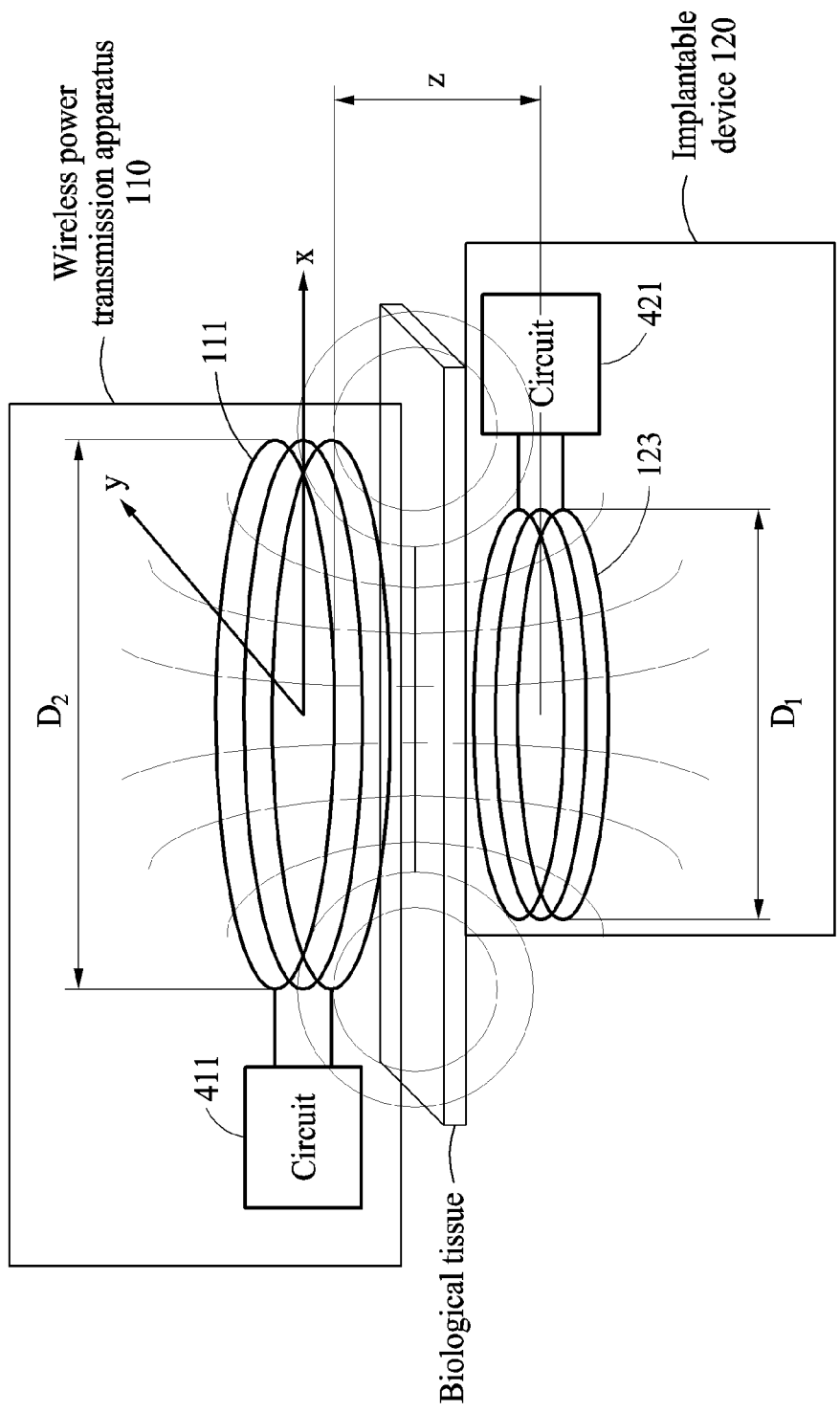
FIG. 4 illustrates an example of a process of transmitting power through coupling between coils.

FIG. 4 illustrates an example of a process of transmitting power through coupling between coils.

The wireless power transmission apparatus 110 and the implantable device 120 transmit or receive an external signal through the coils 111 and 123. The external signal includes, for example, a signal corresponding to a set bandwidth. For example, the wireless power transmission apparatus 110 and the implantable device 120 may transmit or receive a first signal having a first frequency or a second signal having a second frequency through the coils 111 and 123. Received signals are processed by circuits 411 and 421 and are used to adjust a position or to transmit power, as described above.

The wireless power transmission apparatus 110 transmits power to the implantable device 120 via magnetic coupling between the coils 111 and 123. A power transmission efficiency may be determined based on a coupling coefficient between the coils 111 and 123 that are magnetically coupled. The coupling coefficient between the coils 111 and 123 may be determined based on, for example, a characteristic of a biological tissue between the coils 111 and 123, a distance z between the coils 111 and 123, positions (x, y) of the coils 111 and 123, a size D2 of the coil 111, and/or a size D1 of the coil 123. Accordingly, for a high efficiency of a wireless power transmission, a relative position between the wireless power transmission apparatus 110 and the implantable device 120 is important.

Because it is difficult to visually identify a position of the implantable device 120, a position of the wireless power transmission apparatus 110 may be misaligned. The wireless power transmission apparatus 110 and the implantable device 120 may be adjusted to relative positions based on the different frequencies, and thus an efficiency of the wireless power transmission may be increased.

Figure 5:
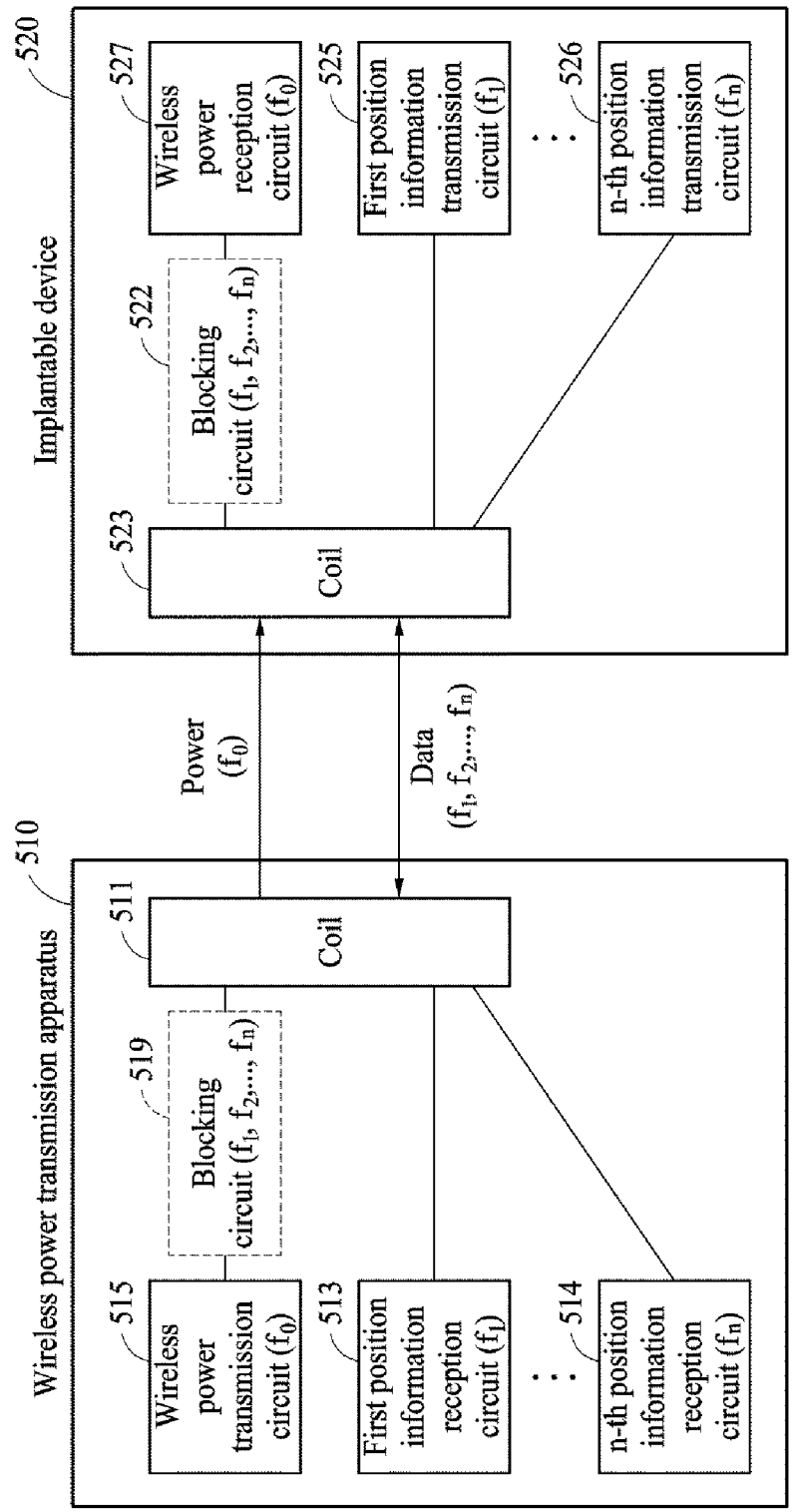
FIG. 5 illustrates an example of a configuration of a wireless power transmission system using additional frequencies.

FIG. 5 illustrates an example of a configuration of a wireless power transmission system using additional frequencies.

The wireless power transmission system of FIG. 5 includes a wireless power transmission apparatus 510 and an implantable device 520 that use at least three frequencies.

Referring to FIG. 5, the wireless power transmission apparatus 510 includes a coil 511, a first position information reception circuit 513 through an n-th position information reception circuit 514, and a wireless power transmission circuit 515. The wireless power transmission apparatus 510 may further include a blocking circuit 519. Although not shown, wireless power transmission apparatus 510 may further include a control circuit and implantable device 520 may further include a power management circuit and a battery, as shown in FIG. 1.

The n-th position information reception circuit 514 receives a third signal having a third frequency from the implantable device 520. The third signal may be associated with a position adjustment, and n is an integer and may denote a number of position information reception circuits corresponding to different frequencies. The first position information reception circuit 513 through the n-th position information reception circuit 514 may receive signals corresponding to different frequencies, for example, frequencies $f_1$ through $f_n$. The blocking circuit 519 blocks a current caused to flow by the signals corresponding to the frequencies $f_1$ through $f_n$ from being transmitted to the wireless power transmission circuit 515.

The implantable device 520 includes a coil 523, a first position information transmission circuit 525 through an n-th position information transmission circuit 526, and a wireless power reception circuit 527. Also, n denotes a number of position information transmission circuits corresponding to different frequencies. The implantable device 520 may further include a blocking circuit 522. The n-th position information transmission circuit 526 transmits the third signal to the wireless power transmission apparatus 510. The first position information transmission circuit 525 through the n-th position information transmission circuit 526 transmit the signals corresponding to the frequencies $f_1$ through $f_n$.

Because a straightness of an electromagnetic wave increases as a frequency increases through the air, a signal may be transferred a further distance. When an electromagnetic wave penetrates a biological tissue, a penetration ratio of a frequency increases based on characteristics of the biological tissue. The wireless power transmission apparatus 510 uses the third frequency that is different from a first frequency and a second frequency. The first frequency and the third frequency used for position adjustment may have sensitivities more suitable for positions in different ranges.

In an example, when the third frequency is greater than the first frequency, the third frequency is suitable for a position adjustment at a distance greater than that of the first frequency. In another example, when a penetration ratio of the third frequency for a biological tissue is greater than that of the first frequency, the third frequency is also suitable for a position adjustment at a distance greater than that of the first frequency. That is, the wireless power transmission apparatus 510 may use the third frequency to be able to adjust a position in a range in which it is difficult to adjust the position based on, for example, the first frequency.

Figure 6:
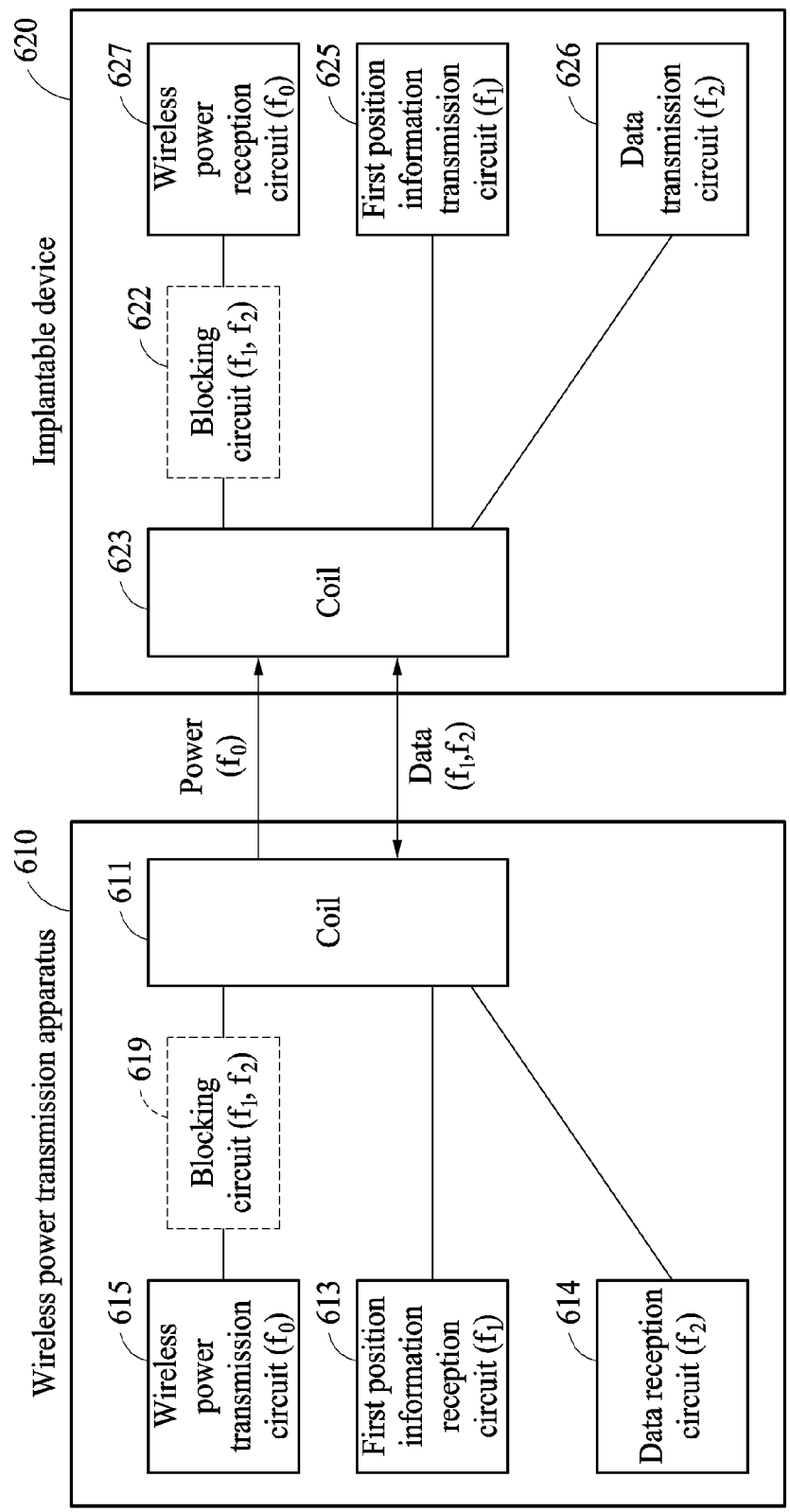
FIG. 6 illustrates an example of a configuration of a wireless power transmission system for exchanging data using an additional frequency.

FIG. 6 illustrates an example of a configuration of a wireless power transmission system for exchanging data based on an additional frequency.

The wireless power transmission system of FIG. 6 includes a wireless power transmission apparatus 610 and an implantable device 620 that use a fourth frequency associated with a data transmission. Accordingly, the wireless power transmission system may transmit data that is independent of position information while performing a wireless power transmission and a position adjustment to assist the wireless power transmission.

Referring to FIG. 6, the wireless power transmission apparatus 610 includes a coil 611, a first position information reception circuit 613, a data reception circuit 614 and a wireless power transmission circuit 615. The wireless power transmission apparatus 610 may further include a blocking circuit 619. Although not shown, wireless power transmission apparatus 610 may further include a control circuit and implantable device 620 may further include a power management circuit and a battery, as shown in FIG. 1.

The data reception circuit 614 is used to receive a fourth signal of a fourth frequency, for example, a frequency $f_2$, from the implantable device 620. The fourth signal is associated with data other than position information. The data other than the position information may include, for example, biometric information such as an EMG signal, a respiration rate, a skin temperature, a skin conductance, a pulse, a heart rate, a blood oxygen concentration, etc.

The blocking circuit 619 blocks current caused to flow by signals corresponding to different frequencies, for example, frequencies $f_1$ and $f_2$, from being transmitted to the wireless power transmission circuit 615. The first position information reception circuit 613 uses the frequency $f_1$, and the wireless power transmission circuit 615 uses the frequency $f_0$.

Referring to FIG. 6, the implantable device 620 includes a coil 623, a first position information transmission circuit 625, a data transmission circuit 626, and a wireless power reception circuit 627. The implantable device 620 may further include a blocking circuit 622. The data transmission circuit 626 transmits the fourth signal to the wireless power transmission apparatus 610.

Figure 7:
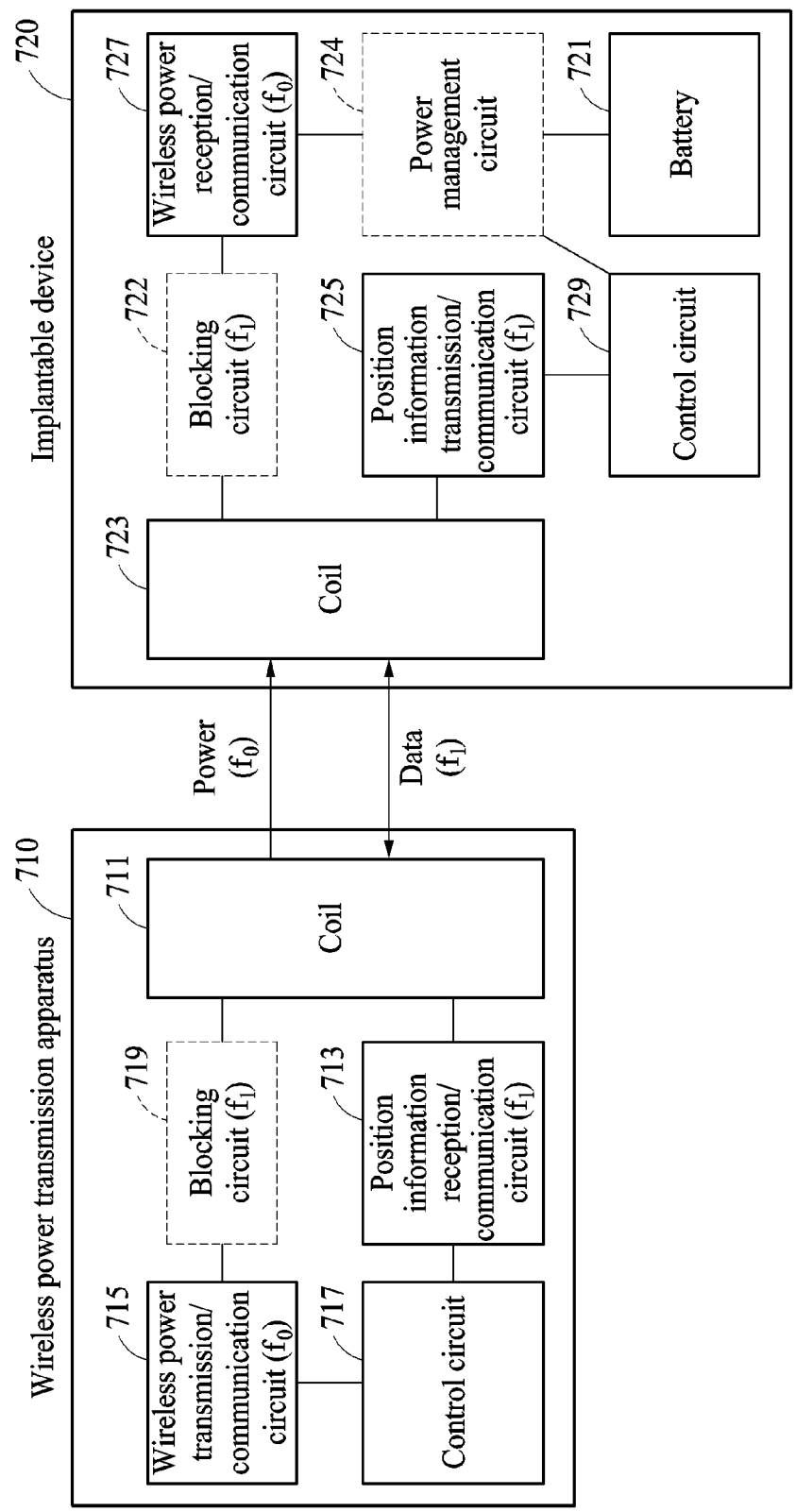
FIG. 7 illustrates an example of a configuration of a wireless power transmission system in which a wireless power transmission circuit and a position information transmission circuit are used as a short-distance communication circuit and a long-distance communication circuit.

FIG. 7 illustrates an example of a configuration of a wireless power transmission system in which a wireless power transmission circuit and a position information transmission circuit are used as a short-distance communication circuit and a long-distance communication circuit.

The wireless power transmission system of FIG. 7 includes a wireless power transmission apparatus 710 and an implantable device 720. The wireless power transmission apparatus 710 and the implantable device 720 perform a short-distance communication and a long-distance communication while performing a wireless power transmission and a position adjustment.

Referring to FIG. 7, the wireless power transmission apparatus 710 includes a coil 711, a position information reception/communication circuit 713, a control circuit 717, a wireless power transmission/communication circuit 715.

For the wireless power transmission, the position information reception/communication circuit 713 receives a first signal from the implantable device 720 and uses the first signal for the position adjustment, and the wireless power transmission/communication circuit 715 transmits a second signal and wirelessly transmits the power. For the short-distance communication and/or the long-distance communication, the position information reception/communication circuit 713 performs the long-distance communication based on the first signal, and the wireless power transmission/communication circuit 715 transmits the second signal and performs the short-distance communication.

The wireless power transmission apparatus 710 may further include a blocking circuit 719. The position information reception/communication circuit 713 uses a frequency $f_1$, and the wireless power transmission/communication circuit 715 uses a frequency $f_0$.

The implantable device 720 includes a coil 723, a position information transmission/communication circuit 725, a control circuit 729, a battery 721 and a wireless power reception/communication circuit 727. The implantable device 720 may further include a blocking circuit 722 or a power management circuit 724.

For the wireless power transmission, the position information transmission/communication circuit 725 transmits the first signal to the wireless power transmission apparatus 710 and uses the first signal for the position adjustment, and the wireless power reception/communication circuit 727 transmits the second signal and wirelessly receives the power. For the short-distance communication and/or the long-distance communication, the wireless power reception/communication circuit 727 performs the short-distance communication based on the second signal, and the position information transmission/communication circuit 725 transmits the first signal and performs the long-distance communication.

The apparatuses, units, modules, devices, and other components illustrated in FIGS. 1, 4, 5, 6 and 7 that perform the operations described herein with respect to FIGS. 2 and 3 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 2 and 3. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A wireless power transmission method, comprising:
   receiving a first signal having a first frequency from an implantable device;
   determining whether a magnitude of the first signal satisfies a first criterion; and
   wirelessly transmitting power to the implantable device based on a second signal having a second frequency in response to the magnitude of the first signal satisfying the first criterion.

2. The wireless power transmission method of claim 1, further comprising:
   re-receiving the first signal from the implantable device in response to the wireless power transmission apparatus being at an adjusted position relative to the implantable device in response to the magnitude of the first signal not satisfying the first criterion.

3. The wireless power transmission method of claim 1, wherein the first frequency is greater than the second frequency.

4. The wireless power transmission method of claim 1, further comprising:
   measuring an impedance variation of a first position information reception circuit in response to a position adjustment signal being received from the implantable device; and
   determining whether the impedance variation satisfies a second criterion,
   wherein the position adjustment signal is generated by the implantable device in response to the transmitted power being less than a third criterion.

5. The wireless power transmission method of claim 4, further comprising:
   interrupting a wireless power transmission in response to the impedance variation not satisfying the second criterion.

6. The wireless power transmission method of claim 4, further comprising:
   outputting a position adjustment request signal indicating a first distance in response to the impedance variation not satisfying the second criterion.

7. The wireless power transmission method of claim 4, further comprising:
   outputting a position adjustment request signal indicating a second distance in response to the impedance variation satisfying the second criterion.

8. A non-transitory computer-readable storage medium storing instructions that, when executed by a processor, cause the processor to perform the wireless power transmission method of claim 1.

9. A wireless power reception method, comprising:
   transmitting a first signal having a first frequency to a wireless power transmission apparatus;
   receiving power from the wireless power transmission apparatus based on a second signal having a second frequency; and
   transmitting a position adjustment signal to the wireless power transmission apparatus in response to the received power not satisfying a criterion.

10. The wireless power reception method of claim 9, wherein the first frequency is greater than the second frequency.

11. The wireless power reception method of claim 9, further comprising:
    determining whether the received power satisfies the criterion.

12. The wireless power reception method of claim 11, further comprising:
    charging a battery of implantable device with the received power in response to the received power satisfying the criterion.

13. A wireless power transmission apparatus, comprising:
    a first position information reception circuit configured to receive a first signal having a first frequency from an implantable device;
    a wireless power transmission circuit configured to transmit a second signal having a second frequency to the implantable device; and
    a control circuit configured to determine whether a magnitude of the first signal satisfies a first criterion and to wirelessly transmit a power to the implantable device based on the second signal in response to the magnitude of the first signal satisfying the first criterion.

14. The wireless power transmission apparatus of claim 13, further comprising:
    a coil configured to transmit and receive the first signal and the second signal through coupling with the implantable device.

15. The wireless power transmission apparatus of claim 13, further comprising:
    a second position information reception circuit configured to receive a third signal having a third frequency corresponding to a position adjustment from the implantable device.

16. The wireless power transmission apparatus of claim 13, further comprising:
    a data reception circuit configured to receive a fourth signal of a fourth frequency comprising data from the implantable device.

17. The wireless power transmission apparatus of claim 13, further comprising:
    a blocking circuit configured to block an interference between the first position information reception circuit and the wireless power transmission circuit.

18. The wireless power transmission apparatus of claim 13, further comprising:
    a blocking circuit configured to open an electrical connection between the first position information reception circuit and the wireless power transmission circuit in response to the first signal being received, and close the electrical connection in response to the second signal being received.

* * * * *